United States Patent [19]

Bergmans

[11] Patent Number: 4,638,661
[45] Date of Patent: Jan. 27, 1987

[54] APPARATUS FOR MEASURING THE VOLUME OF A MEASURING GAS

[75] Inventor: Anthony B. Bergmans, Bilthoven, Netherlands

[73] Assignee: Gould Electronics B.V., Netherlands

[21] Appl. No.: 747,065

[22] Filed: Jun. 20, 1985

[30] Foreign Application Priority Data

Jun. 28, 1984 [NL] Netherlands ............... 8402041

[51] Int. Cl.$^4$ .............................................. G01F 3/34
[52] U.S. Cl. ........................................ 73/237; 73/3; 128/727
[58] Field of Search ................ 73/3, 234, 237; 128/727

[56] References Cited

U.S. PATENT DOCUMENTS 1,061,271  5/1913  Dezendorf ..................... 73/3
2,907,322  10/1959  Hay .

FOREIGN PATENT DOCUMENTS 678508   6/1939   Fed. Rep. of Germany .
1215857  5/1966   Fed. Rep. of Germany .
2406773  9/1974   Fed. Rep. of Germany .
9744451  4/1933   France .
2037056  12/1970  France .
2435242  4/1980   France .
0987399  1/1983   U.S.S.R. ..................... 73/3

Primary Examiner—Herbert Goldstein
Attorney, Agent, or Firm—Pahl, Lorusso & Loud

[57] ABSTRACT

In an apparatus for measuring the volume of a measuring gas, comprising a measuring bell that is movable upwardly and downwardly under influence of the measuring gas and that is suspended from one end of a flexible cable or the like cooperating with a balance device for the measuring bell, the measuring bell together with a stationary body creating a measuring space into which a measuring conduit for the measuring gas communicates, the balance device is constructed in such a manner that it remains operational in a range of measuring bell accelerations that exceed the gravitational acceleration. The balance device exists of a balance weight or a spring element.

9 Claims, 4 Drawing Figures

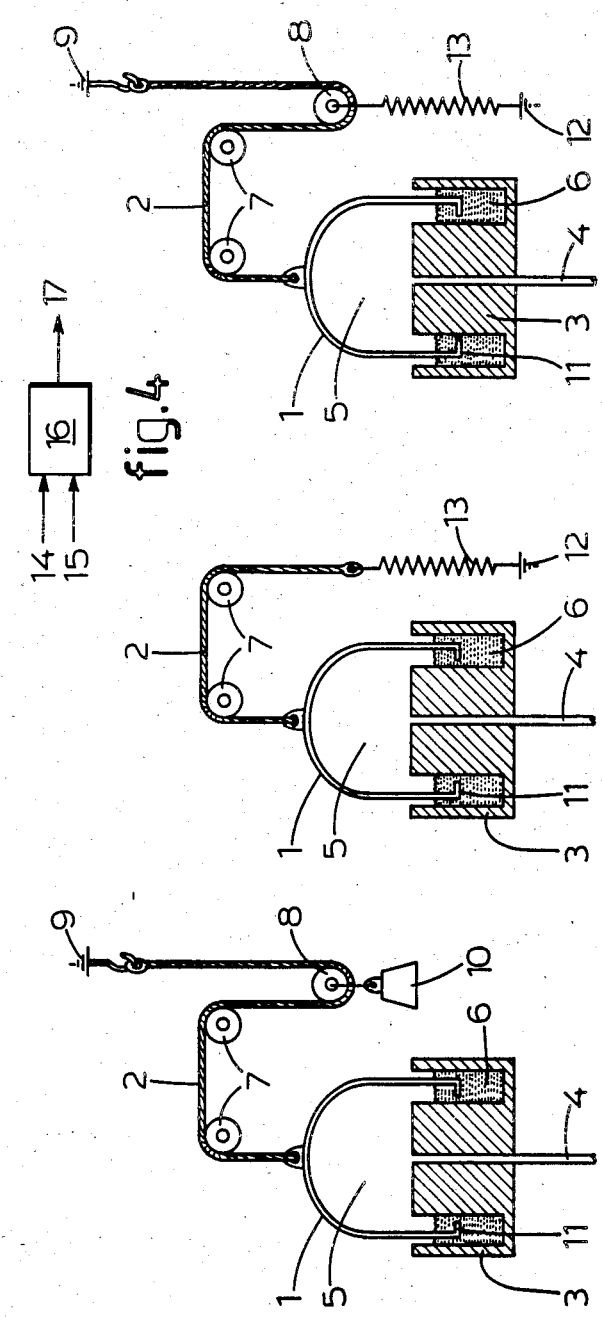

APPARATUS FOR MEASURING THE VOLUME OF A MEASURING GAS

The invention relates to an apparatus for measuring the volume of a measuring gas, comprising a measuring bell that is movable upwardly and downwardly under influence of the measuring gas and that is suspended from one end of a flexible cable or the like cooperating with a balance device for the measuring bell, said measuring bell together with a stationary body creating a measuring space into which a measuring conduit for the measuring gas debouches.

In a known apparatus of this type the balance device exists of a balance weight attached to the other end of the flexible cable or the like, wherein the weight thereof is substantially identical with the weight of the measuring bell. This known apparatus acts mainly as a mass-spring system.

An application of such an apparatus is formed by the so-called spirometer that is often used during medical examinations. With a spirometer the volume of expired air can be measured whereafter this volume can be represented in different ways as a function of other quantities. The shape of this function is an indication for several dysfunctions of the lung function. In an often used lung function test the volume of the expired air is plotted out against the delivery. The course has a characteristic shape, wherein especially the range with the maximum delivery values is of importance for a correct diagnosis. Because extremely high delivery values, e.g. 12 lit/sec, are reached within a very short time, the measuring bell experiences large vertical accelerations which, in the above-mentioned range, can lead to an undesired behaviour of the system that is constituted of the measuring bell and the balance weight. Theoretically the balance weight will loose its effect when the vertical, upwardly directed, acceleration of the measuring bell exceeds the gravitational acceleration. In practice this limit already can be found by even lower accelerations of the measuring bell. In these cases the system looses its mass-spring system character.

The undesired behaviour of the system thus caused, particularly vibrations, leads to a disturbance of the representation of the lung function making it impossible to diagnose correctly.

The maximum delivery value by which the system still functions correctly and continues to act as a mass-spring system can be raised by increasing the area below the measuring bell. As a result a certain delivery value will cause a smaller acceleration of the measuring bell than it would do if the measuring bell would have a smaller area. However, a major disadvantage of this solution is, that the measuring accuracy of the apparatus decreases thereby.

It is an object of the invention to provide an apparatus for measuring the volume of a measuring gas of the type referred to above that also during fast volume changes (high delivery values) continues to act as a mass-spring system and that further has a high accuracy.

Therefore, the apparatus according to the invention is characterized in that the balance device is constructed in such a manner that it remains operational in a range of measuring bell accelerations that exceed the gravitational acceleration.

Now it is possible to give the measuring bell a small area while obtaining a high measuring accuracy without loosing the mass-spring system character.

According to a convenient embodiment of the apparatus according to the invention the other end of the flexible cable or the like is attached to a fixed point, wherein the balance device comprises a balance weight that, by means of a free pulley or the like, is suspended from a free hanging loop that is formed by the cable or the like.

A displacement of the measuring bell now results in a displacement of the balance weight being half as large. Apart from that, for an equilibrium this balance weight substantially has to be twice as high as the weight of the measuring bell. The accelerations of the balance weight are also just half as large as the accelerations of the measuring bell so that the operational range of the apparatus has been doubled.

In another preferred embodiment of the apparatus according to the invention the other end of the flexible cable or the like is attached to a spring element that is attached to a fixed point.

However, it is also possible that the other end of the flexible cable or the like is attached to a fixed point, wherein the balance device comprises a spring element that, by means of a free pulley or the like, is tensioned between a loop formed by the cable or the like and a second fixed point.

Thus in a convenient way use is made of a spring element, wherein the combination with the pulley results in the fact that the system in an advantageous way acts as a mass-spring system.

By considering this apparatus as being a mass-spring system, accurate measuring results are obtained. The spring of this mass-spring system is constituted by the compressed gas below the measuring bell. The spring constant of this spring is not constant so that it is difficult to solve the differential equation describing this system.

When in an extremely advantageous embodiment of the apparatus according to the invention this is provided with an installation for measuring the pressure in the measuring space and for correcting the measured volume by means of this pressure, the measured volume change can be corrected and can be reduced to the real volume change of the measuring gas.

The invention will be explained further hereafter with reference to the drawing showing some embodiments of the apparatus.

FIG. 1 shows schematically an apparatus according to the invention comprising a balance weight being suspended from a free pulley;

FIG. 2 shows schematically an apparatus according to the invention comprising a spring element;

FIG. 3 shows schematically an apparatus according to the invention comprising a spring element being tensioned in a free pulley, and FIG. 4 shows a simple measuring and control diagram to be applied to the apparatus according to the invention.

FIG. 1 schematically shows an apparatus for measuring volumes comprising mainly a measuring bell 1 that is suspended from a flexible cable 2 and a stationary body 3. The measuring bell 1 is movable upwardly and downwardly in vertical direction. This motion is caused by the supply and discharge of a gas through the measuring conduit 4 in the body 3. The measuring conduit 4 debouches in a measuring space 5 that is limited by the measuring bell 1 and the stationary body 3.

The body 3 comprises a roundgoing channel 6 being filled with a fluid, e.g. water. The measuring bell 1 has a shape adapted to this channel 6 and is positioned in the fluid with its lower edge. In this way the measuring space 5 is sealed properly relative to the surroundings, wherein the measuring bell 1 still can move freely in vertical direction relative to the body 3.

The flexible cable 2 is led to a fixed point 9 via several guide rolls 7 and a free pulley 8 and fixed to the same. A balance weight 10 is suspended from the free pulley 8, having such a weight that the measuring bell, dependent on the pressure of the measuring gas in the measuring space 5, takes a certain stationary position, in which the lower edge of the measuring bell 1 is positioned in the fluid in the channel 6 of the body 3 but is not in contact with the body 3. Generally the weight of the balance weight 10 is substantially twice as high as the weight of the measuring bell 1.

When measuring gas 4 is supplied to the measuring space 5 through the measuring conduit 4, the measuring bell 1 will move upwardly. The distance of this upwardly directed motion is a measure for the volume of the supplied gas amount.

At the lower edge of the measuring bell 1 a roundgoing, inwardly directed edge 11 is provided that ensures a damping of the motion of the measuring bell 1. The width of the edge 11 is a measure for the damping. Because this edge 11 is directed inwardly, fluid level differences are compensated by the pressure below the measuring bell 1. For, an overpressure in the measuring space 5 results in a descent of the fluid level at the inner side of the measuring bell 1. Meanwhile, however, the measuring bell 1 is moved upwardly so that the inwardly directed edge 11 as it were propels the fluid at the innerside of the measuring bell 1 upwardly against the descent mentioned before, so that a compensation occurs.

FIG. 2 shows an embodiment of the apparatus according to the invention, wherein a draw spring 13 is provided between the flexible cable 2 and a fixed point 12. This draw spring 13 has a spring constant that is substantially constant over its total operational range.

The embodiment according to FIG. 3 constitutes a combination of the embodiments from FIG. 1 and FIG. 2. The end of the cable is secured to a fixed point 9, wherein a draw spring 13 is provided between a free pulley 8 and another fixed point 12.

In the three embodiments shown the apparatus can be used with higher accelerations of the measuring bell than the known apparatus. The behaviour of the system using the apparatus according to the invention corresponds better with the behaviour of a mass-spring system, so that diagnosing can be more reliable because the motion of the measuring bell 1 corresponds more accurate with the volume changes of the measuring gas.

FIG. 4 shows a diagram for a simple measuring and control apparatus making it possible to carry out corrections on the measured volumes. The inputs 14 and 15 provide the signals coming from sensors and relating to the displacement of the measuring bell 1 or the pressure in the measuring space 5, respectively. In the processor 16 with the aid of the measured pressure 15 a correction is carried out on the volume defined by the displacement of the measuring bell 1. This corrected volume value is delivered via the output 17 for a further processing.

The invention is not limited to the embodiments described above but can be varied widely within the scope of the invention.

I claim:

1. An apparatus for measuring the volume of a gas comprising:
    a stationary body having a circumferential channel for receiving a fluid;
    a measuring bell movable upwardly and downwardly in vertical direction which is suspended into the circumferential channel so that a measuring space is formed between the measuring bell and the stationary body;
    a measuring conduit extending axially through the stationary body wherein the conduit communicates at one end with the measuring space and at the other end with the gas to be measured;
    a flexible cable for suspending the measuring bell into the circumferential channel which is fixed at one end to the top of the measuring bell and at the other end to a fixed point wherein the flexible cable passes over at least two guide rolls before it terminates at the fixed point;
    a free pulley supported by the flexible cable between the at least two guide rolls and the fixed point end of the cable wherein the free pulley sits in a free hanging loop of the cable between the guide rolls and the fixed point; and
    a balance weight supported by the free pulley having a weight sufficient to position the circumferential edge of the bell in the circumferential channel of the body but not in contact with the body.

2. The apparatus as recited in claim 1 wherein the measuring bell further includes a lower circumferential edge which projects perpendicularly with respect to the vertical direction of movement of the measuring bell.

3. The apparatus as recited in claim 1 wherein the circumferential edge is directed inwardly.

4. The apparatus as recited in claim 1 further comprising:
    means for measuring the volume of a gas which has been introduced through the measuring conduit into the measuring space which is responsive to the vertical axial movement of the measuring bell; and
    means for measuring the pressure in the measuring space and for correcting the volume measured by means of this pressure.

5. An apparatus for measuring the volume of a gas comprising:
    a stationary body having a circumferential channel for receiving a fluid;
    a measuring bell movable upwardly and downwardly in vertical direction which is suspended into the circumferential channel so that a measuring space is formed between the measuring bell and the stationary body;
    a measuring conduit extending axially through the stationary body wherein the conduit communicates at one end with the measuring space and at the other end with the gas to be measured;
    a flexible cable for suspending the measuring bell into the circumferential channel which is fixed at one end to the top of the measuring bell and at the other end to a fixed point wherein the flexible cable passes over at least two guide rolls before it terminates at the fixed point;
    a free pulley supported by the flexible cable between the at least two guide rolls and the fixed point end of the cable wherein the free pulley sits in a free hanging loop of the cable between the guide rolls and the fixed point; and a tension spring attached at one end to the free pulley and at the other end to a fixed point having a tension sufficient to position the circumferential edge of the bell in the circumferential channel of the body but not in contact with the body.

6. The apparatus as recited in claim 5 wherein the tension spring has a spring constant that is substantially constant along its total working range.

7. The apparatus as recited in claim 5 wherein the measuring bell further includes a lower circumferential edge which projects perpendicularly with respect to the vertically axial direction of motion of the measuring bell.

8. The apparatus as recited in claim 5 wherein the circumferential edge is directed inwardly.

9. The apparatus as recited in claim 5 further comprising:

means for measuring the volume of a gas which has been introduced through the measuring conduit into the measuring space which is responsive to the vertical axial movement of the measuring bell; and means for measuring the pressure in the measuring space and for correcting the volume measured by means of this pressure.

* * * * *